US008864799B2

(12) United States Patent
Kraus (10) Patent No.: US 8,864,799 B2
(45) Date of Patent: Oct. 21, 2014

(54) ROD CONNECTOR (76) Inventor: Kilian Kraus, Werneck (DE)

( * ) Notice: Subject to any disclaimer, the term of this patent is extended or adjusted under 35 U.S.C. 154(b) by 0 days.

(21) Appl. No.: 13/493,069

(22) Filed: Jun. 11, 2012

(65) Prior Publication Data

US 2012/0253397 A1 Oct. 4, 2012

Related U.S. Application Data (63) Continuation of application No. PCT/EP2010/068969, filed on Dec. 6, 2010.

(30) Foreign Application Priority Data

Dec. 10, 2009 (DE) .......................... 10 2009 056 890

(51) Int. Cl.
*A61B 17/70* (2006.01)
*A61B 17/80* (2006.01)

(52) U.S. Cl.
CPC ......... *A61B 17/7052* (2013.01); *A61B 17/8042* (2013.01); *A61B 17/7049* (2013.01)
USPC ........... 606/253; 606/250; 606/251; 606/252; 606/278

(58) Field of Classification Search
USPC .......... 606/248, 249, 250–253, 276, 277, 278
See application file for complete search history.

(56) References Cited

U.S. PATENT DOCUMENTS

| 7,029,474 | B2 | 4/2006 | Richelsopf et al. |
| 7,066,938 | B2 | 6/2006 | Slivka et al. |
| 7,717,940 | B2 * | 5/2010 | Woods et al. ................. 606/253 |
| 8,292,924 | B2 * | 10/2012 | Neary et al. .................... 606/250 |
| 8,353,934 | B2 * | 1/2013 | Drewry et al. ................. 606/250 |
| 2003/0114853 | A1 * | 6/2003 | Burgess et al. ................. 606/61 |
| 2005/0228377 | A1 * | 10/2005 | Chao et al. ...................... 606/61 |
| 2006/0247626 | A1 * | 11/2006 | Taylor et al. .................... 606/61 |
| 2006/0271045 | A1 | 11/2006 | Hubbard et al. |
| 2006/0271051 | A1 * | 11/2006 | Berrevoets et al. ............. 606/61 |
| 2007/0016197 | A1 | 1/2007 | Woods et al. |
| 2008/0109039 | A1 | 5/2008 | Michielli et al. |
| 2008/0306538 | A1 * | 12/2008 | Moore et al. .................. 606/250 |

(Continued)

FOREIGN PATENT DOCUMENTS

| JP | 7241299 A | 9/1995 |
| WO | 2007/133938 A2 | 5/2007 |
| WO | 2008/140756 A2 | 5/2008 |
| WO | 2008/140756 A3 | 5/2008 |

*Primary Examiner* — Jerry Cumberledge
(74) *Attorney, Agent, or Firm* — Laurence A. Greenberg; Werner H. Stemer; Ralph E. Locher (57) ABSTRACT

A rod connector for transversely connecting two vertebral column rods has two clamps and a transverse bridge that fixes the clamps to each other. The clamps have a spring device with a spring force that is low enough to allow the clamp to be manually snapped onto the vertebral column rod, to be slid onto the same in the installed state, and to be released from same. An attaching device for the clamp, which is independent of the spring device, generates a retaining force that is high enough to solidly attach the clamp on the vertebral column rod in the installed state. The transverse bridge has a connection part with a frame for receiving a first branch connected to one clamp and with a ball rotatably mounted in the frame and having a second branch pass therethrough that connects to another clamp.

11 Claims, 11 Drawing Sheets

(56) References Cited

U.S. PATENT DOCUMENTS

2010/0204733 A1* 8/2010 Rathbun et al. ............... 606/251
2010/0241168 A1* 9/2010 Franck et al. ................. 606/250
2011/0040330 A1* 2/2011 Sheffer ......................... 606/249
2013/0006307 A1* 1/2013 Robinson et al. ............. 606/252

* cited by examiner

ROD CONNECTOR

CROSS-REFERENCE TO RELATED APPLICATION

This application is a continuation, under 35 U.S.C. §120, of copending international application No. PCT/EP2010/068969, filed Dec. 6, 2010, which designated the United States; this application also claims the priority, under 35 U.S.C. §119, of German patent application No. DE 10 2009 056 890.5, filed Dec. 10, 2009; the prior applications are herewith incorporated by reference in their entirety.

BACKGROUND OF THE INVENTION

Field of the Invention

The invention relates to a rod connector for the transverse connection of two vertebral column rods.

Orthopedic operations are performed on patients in order, among other things, to correct the profile of the vertebral column. To do this, two vertebral column rods are generally placed to the left and right of the vertebral column during an operation and are secured, with the aid of various hooks or screws, to the vertebral column or to the vertebrae. In order also to fix both vertebral column rods securely in relation to each other, so-called rod connectors (also called rod-to-rod connectors) are known.

U.S. Pat. No. 7,029,474 B2 describes a rod connector which is fixed on the rods in such a way that a clamping jaw is pressed against the rod with the aid of a screw.

U.S. Pat. No. 7,066,938 B2 describes an alternative rod connector which is snapped onto the rod in the manner of an expandable bracket.

SUMMARY OF THE INVENTION

It is accordingly an object of the invention to provide a rod connector which overcomes various disadvantages of the heretofore-known devices and methods of this general type and which provides for an improved rod connector.

With the foregoing and other objects in view there is provided, in accordance with the invention, a rod connector for a transverse connection of two vertebral column rods, the rod connector comprising:

first and second clamps each for partially enclosing and securing a respective vertebral column rod in an assembly state thereof;

a transverse bridge for fixing the clamps relative to each other, the transverse bridge including a first branch mounted on the first clamp, a second branch mounted on the second clamp, and a connection part connecting the first and second branches;

the connection part having a frame for receiving the first branch, a ball rotatably mounted in the frame and having the second branch pass therethrough, and a locking device acting on the first and second branches;

a spring mechanism for each the clamp, the spring mechanism having a spring force with a value that is low enough to enable the clamp to be snapped manually onto the vertebral column rod, to be displaced thereon in the assembly state, and to be released therefrom; and a fixing mechanism for each the clamp, the fixing mechanism being capable of actuation independently of the spring mechanism and having a holding force high enough to solidly fix the clamp on the vertebral column rod in the assembly state.

In other words, the object of the invention is achieved by a rod connector for the transverse connection of two vertebral column rods where the rod connector comprises two clamps, each partially enclosing and securing a respective vertebral column rod in an assembly state. The assembly state designates the state when the rod connector is mounted on the vertebral column rods; the first clamp then encloses the first vertebral column rod, the second clamp the second vertebral column rod. The clamps in this case only partially enclose the vertebral column rods, i.e. not around the entire circumference, but nevertheless to such an extent that the clamps are secured safely on the vertebral column rod.

The rod connector also comprises a transverse bridge, which fixes the location of the clamps relative to each other. The transverse bridge can, for example, be of a rigid construction, i.e. the clamps have a fixed orientation to each other in relation to the vertebral column rods that are to be enclosed, for example with the clamps being oriented with respect to each other in such a way that enclosed vertebral column rods always run parallel in the assembly state. Generally, however, the transverse bridge will be adjustable in terms of the relative position of the clamps and will be able to be locked in any desired relative position. Thus, by means of one and the same rod connector, vertebral column rods can be fixed in relation to each other in different relative positions.

The restriction to two clamps is not strictly necessary. It would also be conceivable to use rod connectors with three or more clamps, which are then each fixed in position relative to one another by the transverse bridge, and then either one vertebral column rod is intended to be locked particularly securely by two clamps being snapped onto it, or else a third vertebral column rod is fixed by a single rod connector relative to two other rods.

The rod connector also comprises a spring mechanism for the clamp. In other words, the clamp has a resilient design, so as to be snapped onto the vertebral column rod or also removed again from the latter. For example, when the clamp is being mounted on the vertebral column rod, the jaws of the clamp must spring apart, and, when the clamp is in the fully mounted state, the jaws must spring closed again, enclosing the vertebral column rod. The clamp bears, in particular with the spring force, in a frictionally engaged manner on the vertebral column rod. According to the invention, the spring force is so low that the clamp can be snapped manually, e.g. by an operating surgeon, onto the vertebral column rod, can be easily displaced thereon in the assembly state, and can also be released manually from the vertebral column rod. The displaceability here denotes an axial displaceability and also a displaceability in the circumferential direction of the vertebral column rod, which is generally in the shape of a cylinder.

According to the invention, the rod connector also additionally has a fixing mechanism for the clamp. This fixing mechanism can be actuated independently of the spring mechanism. When the fixing mechanism is actuated, it generates an additional holding force, which the clamp exerts on the vertebral column rod, which force is added to or replaces the spring force. The holding force is such that the clamp is fixed solidly on the vertebral column rod in the assembly state. In this context, fixed solidly means that a displacement or rotation of the clamp on the vertebral column rod is no longer possible; neither manually, nor later on through the use of the vertebral column rod in the patient.

In other words, according to the invention, a rod connector with a dual function is provided. The first is an adjustment function: By virtue of the spring mechanism, the rod connector is designed such that, although it is snapped captively onto the vertebral column rods during an operation, it nevertheless permits adjustment through displacement, movement, possible unsnapping and then engagement at another position. However, the rod connector is already held with a certain force on the vertebral column rods, such that a safe, simple and reliable adjustment to a defined final position is possible.

The second is a fixing function: Only when the desired final position is found is the fixing mechanism actuated and the vertebral column rod finally fixed in the position in question. In the case of an adjustable transverse bridge, the final fixing also concerns the final fixing of the transverse bridge, i.e. the final fixing of the relative position of the clamps to each other.

In a preferred embodiment, the clamp has a main support, with a stationary clamping jaw, and also a spring jaw mounted resiliently on the main support. The resilient mounting is effected by the spring mechanism, which mounts the spring jaw resiliently with respect to the main support or clamping jaw. The fixing mechanism then locks the spring jaw against the clamping jaw upon actuation thereof, such that the spring jaw against the main support or clamping jaw can no longer spring away from a final position fixing the vertebral column rod.

In a variant of this embodiment, the spring mechanism is a spring bridge connecting the spring jaw to the main support. The spring bridge thus has a dual function, namely, on the one hand, connecting the spring jaw to the main support, in order, on the other hand, to generate the above-described spring action of the clamp. A separate spring element is then no longer necessary for the spring-loading of a spring jaw, mounted for example in an articulated manner, on the main support.

In addition, the following is thus possible: In another variant of this embodiment, spring jaw, spring bridge and main support are formed in one piece. The spring bridge, which connects a solid spring jaw to a solid main support, is adapted to the material of the clamp, for example made sufficiently thin. For example, the spring bridge is a connecting bridge between spring jaw and main support and has been cut out from a metal in the manner of a leaf spring.

In another variant of this embodiment, the spring jaw and/or the spring bridge is cut out from the main support. The spring property of the spring part can be determined simply by the dimensions of the cutout. In addition, connection techniques for formerly individual parts are not needed in order to connect them, e.g. weld them, in one piece again.

In another embodiment of the invention, main support and spring jaw each have a form-fit element. The two form-fit elements have play between each other in respect of the spring mechanism. However, the form-fit elements can be moved into each other with a form fit by the fixing mechanism. In other words, the form-fit elements are not to be brought into engagement with each other in respect of the spring properties of the clamp, i.e. by simple spring-back of the clamp. Until the clamp is finally fixed, the form-fit elements do not engage in each other. A free spring movement of the clamp is possible. When the clamp is finally fixed, the form-fit elements engage in each other and ensure a secure and permanent hold of the clamp on the vertebral column rod.

In a variant of this embodiment, the form-fit elements, on their faces directed toward each other, have an at least approximately S-shaped matching form. In other words, a gap present between main support and spring jaw in the area of the form-fit elements is S-shaped. By deformation or movement of the spring jaw with the aid of the fixing mechanism, both structural parts are moved toward each other such that the form-fit elements touch. The S-shaped matching form here affords the possibilities of form-fit engagement of the respective two U-shaped or arc-shaped parts of the S.

In a preferred embodiment of the invention, the fixing mechanism comprises a form-fit element that prevents the pivoting-open of the clamp. By means of a corresponding form-fit element, a movement of the clamp in respect of its pivoting open is in fact prevented by a form fit, such that the clamp remains finally fixed on the vertebral column rod. In other words, a form fit then prevents the play of the clamp otherwise provided by the spring element. In conjunction with the abovementioned design of a main support with a spring jaw, a possible example of a form-fit element would be a form-fit element that supports the spring jaw relative to the main support with a form fit. The form-fit element is preferably held captively on the clamp by a loss prevention device.

In a variant of this embodiment, the form-fit element is a threaded element acting on the clamp. In other words, by actuation of the threaded element, a form fit and in particular a high pressing force of the clamp on the vertebral column rod is generated. For example, the threaded element, starting from a position in which it is at a distance from the spring jaw and thus permits the spring movement of the latter, is screwed in and placed or pressed against the spring jaw, such that the previous spring movement is no longer possible. A threaded element is, for example, a screw, or a threaded pin which is mounted in the main support, bears on the main support and presses against the spring jaw. For example, according to the above, the screw is then held on the main support by a loss prevention device, such that it cannot come loose from the rod connector, even in the state when not locking the clamp.

In a preferred embodiment of the invention, the transverse bridge comprises two branches, each of the branches being mounted respectively on one of the clamps. The transverse bridge also comprises a connection part, through which both branches extend and which has a locking device acting on the two branches. In the case of branches that overlap each other in their axial direction, a degree of freedom can be achieved here for the placing of the connection part. The latter is displaceable in the overlap area of the two branches. The connection part can thus be displaced to a desired position relative to the patient.

In a variant of this embodiment, the locking device is one that generates a locking frictional engagement between branches and connection part. In other words, the two branches here are jammed in the connection part with such a high clamping force that this produces a permanent relative fixing of the two branches and, therefore, of the clamps.

In another variant of the embodiment, the connection part comprises a frame for receiving the first branch, and a ball which is mounted rotatably in the frame and through which the second branch passes. The first branch is here mounted in the frame fixedly, for example, or so as to be axially displaceable along the longitudinal axis of the branch. By means of the second branch being mounted in the ball and the latter being rotatable, the second branch can be tilted, twisted and rotated relative to the first branch, within the range of rotation possibilities of the ball. Generally, an axial displaceability of the second branch in the ball is also possible. The locking device then also locks the ball in the frame and the respective position of the branches in the frame and in the ball. By means of the ball, the second branch can thus rotate, relative to the first branch and to the frame, about the center point of the ball.

In another variant of this embodiment, the ball has a compressible gap for locking the second branch extending through the ball. In other words, the ball is compressed at the gap by the locking device, such that the ball closes firmly with frictional engagement around the second branch passing through it and locks this second branch. In other words, the branch sits between two ball parts separated by the gap, which ball parts are movable toward each other in order to lock the branch with a clamping action.

In another variant of this embodiment, the locking device comprises a clamping element that bears on the frame and that presses the first branch against the ball. Thus, all parts of the locking device and of the transverse bridge are fixed relative to one another by a single clamping element, since, on the one hand, the clamping element presses the first branch against the ball and fixes these relative to each other, and at the same time the first branch is jammed in the ball, as a result of the compression of the latter, and is held in this way. In addition, the ball is also finally pressed against the frame, and all the parts are thus fixed relative to one another. In other words, therefore, the two branches, the ball and the frame are pressed against one another and fixed in the connection part by the clamping element.

Other features which are considered as characteristic for the invention are set forth in the appended claims.

Although the invention is illustrated and described herein as embodied in a rod connector, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying schematic illustrations in the drawing.

DETAILED DESCRIPTION OF THE INVENTION

Figure 1:
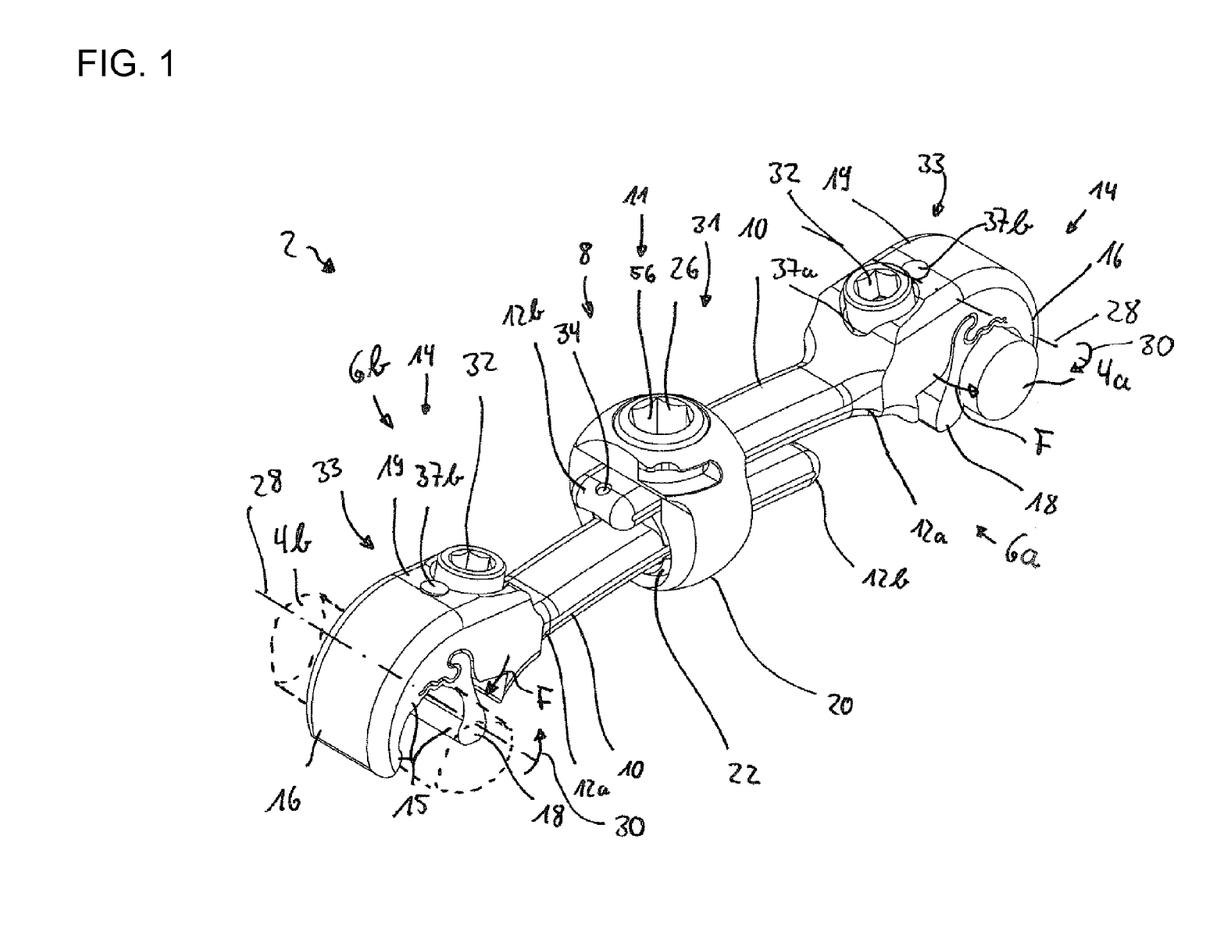
FIG. 1 shows a perspective view of a rod connector mounted on two vertebral column rods.
Figure 2:
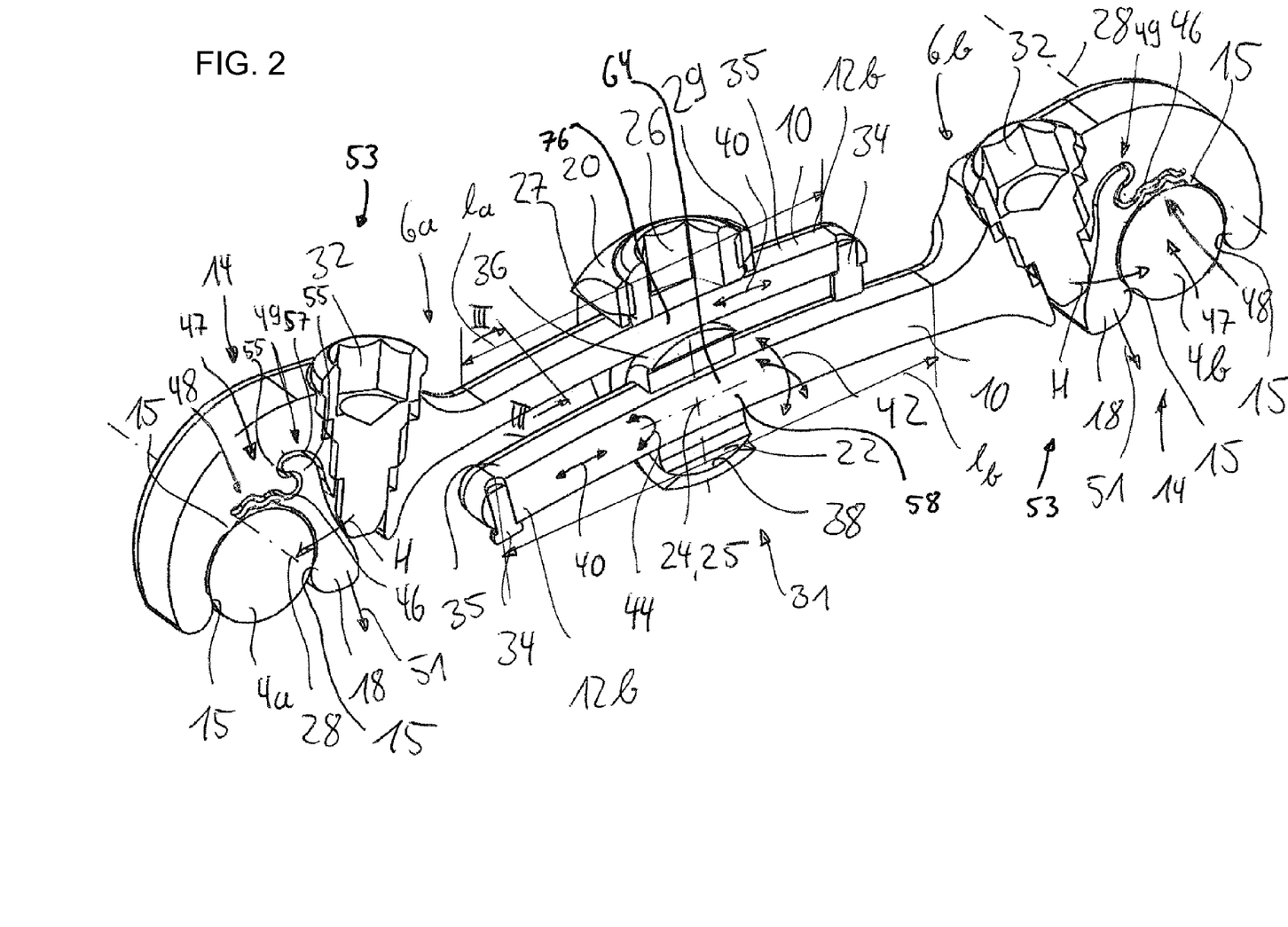
FIG. 2 shows a perspective view of the rod connector from FIG. 1, in a centrally cut longitudinal section.

Referring now to the figures of the drawing in detail and first, particularly, to FIGS. 1 and 2 thereof, there is shown a rod connector 2 or rod-to-rod connector 2, which is mounted on two vertebral column rods 4a,b. The rod connector is made principally in three parts and comprises two brackets 6a,b and a connection part 8. By means of the latter, the brackets 6a,b are variable, in terms of their spatial position relative to each other, in several degrees of freedom and can be fixed relative to each other in a desired spatial position. Each of the brackets 6a,b has a longitudinally extending branch 10, on the respective one end 12a of which a clamp 14 is arranged. The respective other end 12b of the branches 10 lies beyond the connection part 8, i.e. the branches 10 pass through the latter. In other words, the branches 10 are directed toward each other and overlap each other. The branches 10 thus form, together with the connection part 8, a transverse bridge 11, which fixes the location of the two clamps relative to each other.

Each clamp 14 is made up of a clamping jaw 16 and of a spring jaw 18, which is connected resiliently to the clamping jaw 16 and is formed integrally thereon. In other words, the clamping jaw 16 is part of a main support 19, on which the spring jaw 18 is mounted and the branch 10 is securely adjoined.

The connection part 8 comprises a frame 20 and a ball 22 mounted in the latter in the manner of a ball joint. The ball 22 has an outer surface 36, which forms a part of a sphere and whose center point 24 is the ball center point. The frame 20 has, in its interior or in an insert opening 58 (see also FIG. 4), an inner surface 38, which receives the outer surface 36 in the manner of a slide bearing and which is likewise part of a ball surface with the same radius. The center point 25 of the inner surface 38 is once again the corresponding ball center point thereof. Since, as can be seen from FIG. 2 for example, the ball 22 lies in the inner surface 38, in this situation the ball center points 24, 25 coincide concentrically. Outer surface 36 and inner surface 38 thus interact in the sense of a slide pairing and form a ball joint that is rotatable in principle in all directions.

The ball 22 has a receiving space 64 (see FIG. 7) through which the branch 10 of the bracket 6b passes. In the receiving space 64, the branch 10 is guided axially displaceably in the manner of a slide guide only in the direction of the arrow 40. The branch 10 of the bracket 6a is located between ball 22 and frame 20 in a further insert opening or in a receiving space 76 (see FIG. 13) formed between ball 22 and frame 20. The branches 10 and the ball 22 can be fixed relative to each other in terms of their spatial position by tightening of a clamping element 26 in the form of a threaded pin, which is part of the connection part 8. A tool is generally used for this purpose. The clamping element 26 thus forms a locking mechanism 31 for fixing the branches 10 and the connection part 8 in a desired position relative to one another.

The clamping element 26 has a collar 27 at its inner end, i.e. the external thread of the clamping element 26 is not formed or milled all the way to the inner end. In the position shown in FIG. 2, the collar 27 abuts against the inner end 29 of the internal thread formed in a threaded opening 56. Therefore, during assembly of the connection part 8, the clamping element 26 can be screwed into the threaded opening 56 only from the inside, that is to say from the direction of the insert opening 58. After complete assembly of the connection part 8, the clamping element 26 is thus held in such a way that it cannot be lost. The clamping element 26, should it come loose, cannot therefore be lost, either during the handling of the rod connector 2 during an operation or in the state when fitted in the patient.

The force-fit engagement for the fixing is obtained in detail as follows: The clamping element 26 engaging in the frame 20 presses the branch 10 of the bracket 6a against the outer surface 36 of the ball 22 and compresses the latter on account of a gap 66 provided therein (see FIG. 7), such that this presses against the inner branch 10 of the bracket 6b, and the latter in turn clamps the opposite side of the ball 22 against the inner surface 38 of the frame 20.

Since the ball 22 is rotatable about the common center point 24, 25, the following degrees of freedom are obtained for the adjustment of the rod connector 2: The branches 10 are axially movable along the arrows 40 in relation to the connection part 8. In this way, it is possible to compensate for different distances between the vertebral column rods 4a,b. By means of a rotation of the ball 22 in the frame 20 about the center point 24, 25 according to the arrows 42, the longitudinal axes of the branches 10 can be tilted relative to each other between a parallel orientation and a skew orientation. Moreover, by rotation of the ball 22 in the frame 20 about the longitudinal axis of the branch 10 of the bracket 6b in the direction of the arrow 44, it is possible to twist the two brackets 6a,b relative to each other. In this way, it is possible to compensate for all the spatial positions of the vertebral column rods that are conceivable during an operation on a patient or for all the deviations of the vertebral column rods from a parallel arrangement.

The connection part 8 can be moved freely in the direction of the arrows 40 in the overlapping area of the branches 10. If, for example, when the rod connector 2 is fitted in place in an operation, the branches 10 extend between two closely bearing spinous processes of vertebrae, the connection part 8 can be moved from the center toward the left or right side of the vertebral column, so as not to touch or impede the spinous processes.

When the clamp 14 is fitted onto the vertebral column rod 4a,b, the spring jaw 18 pivots about its bearing axis 28 away from the clamping jaw 16 in the direction of the arrow 30, in order to receive the vertebral column rod 4a,b in the clamp 14. As soon as the vertebral column rod 4a,b lies therein, the spring jaw 18 pivots counter to the direction of the arrow 30 back into the position shown. A further component of the brackets 6a,b, namely a fixing element 32 in the form of a threaded pin, is then screwed into the clamp 14, in order to press against the spring jaw 18 and press this against the vertebral column rod 4a,b and press the latter against the clamping jaw 16 and finally fix it. Similarly to the above, the fixing element 32 is also equipped with a loss prevention device 33, such that it cannot come loose from the rest of the rod connector 2 during handling or after being placed in the patient (see also FIG. 15). For the sake of clarity, the loss prevention device is not shown in FIG. 2. For this purpose, the fixing element 32 carries a radially protruding collar 37a, and, after introduction of the fixing element 32, a stop pin 37b is introduced, e.g. welded, into the main support 17. When the fixing element 32 is unscrewed, the collar 37a strikes against the stop pin 37b and prevents release of the fixing element 32 from the respective bracket 6a,b.

Alternatively, in a manner not shown, the loss prevention device 33 can also conceivably comprise a resilient latching lug, inserted into the clamp 14, and an abutment on the fixing element 32. The latching connection then snaps into engagement the first time the fixing element 32 is screwed in, such that the latter is then no longer removable.

The clamps 14 for securing on the vertebral column rod 4a,b thus have a dual function. The first is a spring function as follows: A partial cutout 46 in part of the one-piece clamp 14 creates the movable spring jaw 18. The remaining part of the clamp 14 forms the stationary clamping jaw 16. By virtue of the spring jaw 18, the clamp 14 can be snapped onto a vertebral column rod 4a,b and can also be released from the latter again. A spring force F, with which the clamp 14 acts on the vertebral column rod 4a,b, is so low that it is sufficient, for example, for a rough or displaceable mounting of the rod connector 2 on the vertebral column rods 4a,b, such that said rod connector 2 cannot at first slip out of position or slide off the vertebral column rod 4a,b. However, the spring force F still allows the clamp 14 to be held on the vertebral column rod 4a,b such that it can be twisted or displaced manually or can even be removed again. No tools are therefore necessary for this purpose.

The clamps 14 bear on the vertebral column rods 4a,b via in each case three radially inwardly protruding beads 15 that extend parallel thereto. These beads 15 provide a linear bearing of the clamp 14 on the vertebral column rods 4a,b, such that the surface pressure forces that occur upon final fixation are kept as low as possible. Vertebral column rods 4a,b made of titanium are extremely pressure-sensitive, for example, and can be easily damaged when a clamping screw bears directly on them, as is known in the prior art. This situation is thus avoided.

The spring jaw 18 is connected to the clamp via a spring bridge 48 and a hinge 49. Both parts are produced in one piece with the clamp 14 by means of the cutout 46. The hinge 49 is formed by two form-fit elements 55, which lie opposite each other and are separated by a gap 57, and serves for the final fixation, namely when the hinge parts thereof are pressed with a form fit into each other by tightening of the fixing element 32. The spring bridge 48 serves for the resiliency of the spring jaw 18, such that the latter, during the snapping of the clamp onto the vertebral column rod 4a,b, springs back, and, in the snapped-on position, fixes the vertebral column rod 4a,b between itself and the clamping jaw 16 with a spring force F. The spring bridge 48 thus forms a spring mechanism 47. The spring bridge 48 has an undulating shape and is therefore also extensible in its longitudinal direction. Thus, when the fixing element 32 is tightened, the displacement of the spring jaw 18 is taken up, if the hinge 49 slides into the form fit, i.e. a stretching or breaking-off of the spring bridge 48 is prevented.

At their respective ends 12b, the branches 10 are provided with a pin 34 which, after the assembly of the rod connector 2, is pressed into the branches 10, welded to the upper face 35 thereof and then trimmed. Because of the pins 34, it is then no longer possible to remove the branches 10 from the connection part 8. This avoids the rod connector 2 breaking up into individual parts during handling.

The position of the bearing axes 28 is at the end of the cutout 46. The final fixing on the vertebral column rod 4a,b represents the second of the dual functions of the clamps 14. Manual displacement or release is then no longer possible. In the final fixing, i.e. when the fixing element 32 is tightened using a tool (not shown), the spring jaw 18 is forced in the direction of the arrow 51, as a result of which the hinge 49 comes into abutment or form fit. In other words, in the area of the hinge 49, the spring jaw 18 is pressed on in the body of the clamp 14. The undulating structure of the spring bridge 48 has the effect that this stretches and provides the required length compensation for the displacement of the spring jaw 18 in the direction of the arrow 51. As a result of this, the clamp is pressed with a holding force H against the vertebral column rod 4a,b, and this prevents release and displacement. Fixing element 32 and hinge 49 thus form a fixing device 53 for the final fixing.

The branch 10 of the bracket 6b has a greater length $l_b$ than the branch 10 of the bracket 6a, which has the length $l_a$. Thus, when the branches 10 are moved along the arrows 40, the greatest possible range of distance between connectable vertebral column rods 4a,b can be covered. For the achievable minimum distance, the ends 12b, on the one hand, lie in proximity to the fixing element 32 of the bracket 6b and, on the other hand, in proximity to the spring jaw 18 of the bracket 6a. Since the respective spring jaw 18 is farther than the fixing element 32 from the connection part 8, the branch 10 of the bracket 6b can also be designed with a greater length $l_b$. This additional length difference $l_b$-$l_a$ provides an extended maximum possible distance for vertebral column rods 4a,b if the branches 10 are drawn out until their pins 34 abut against the connection part 8.

Figure 3:
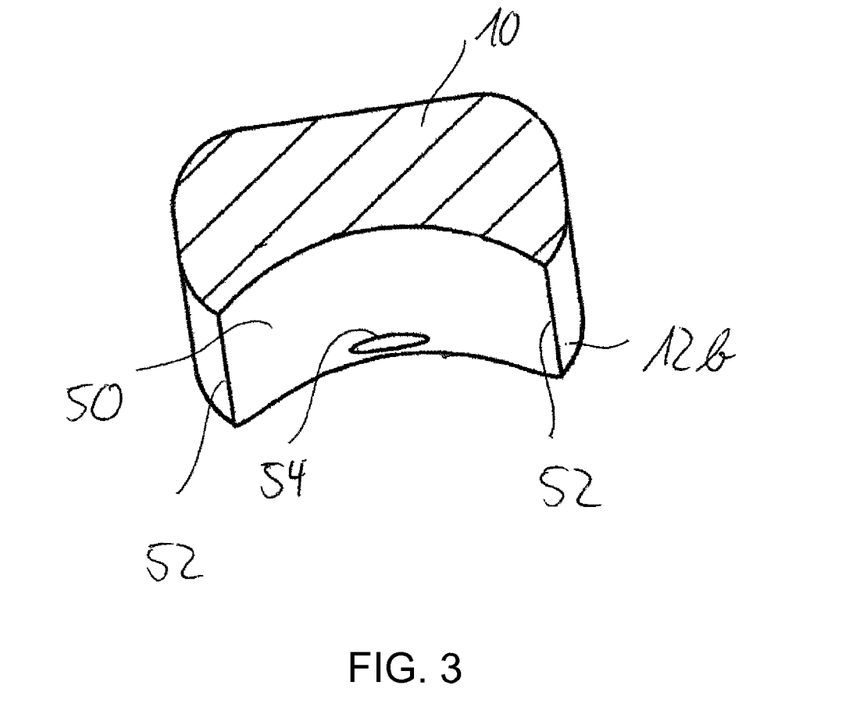
FIG. 3 shows a perspective view of the branch of the unassembled bracket from FIG. 1 in transverse section along the line III-III.

FIG. 3 shows a cross section along the line III-III through the branch 10 of the bracket 6a, i.e. looking in the direction of the end 12b thereof. The underside 50 of the branch 10 directed toward the ball 22 or toward the outer surface 36 thereof has a cross section shaped as an arc of a circle, in order to bear on the spherical outer surface 36. The circle radius of the underside 50 is chosen here to match the sphere radius of the ball 22, in order to achieve a surface pressure between branch 10 and ball 22.

FIG. 3 shows the bracket 6a in the as yet unassembled state, i.e. before it has been inserted into the connection part 8. Therefore, an opening 54 can still be seen at the end 12b, which opening 54 later serves to receive the pin 34.

Figure 4:
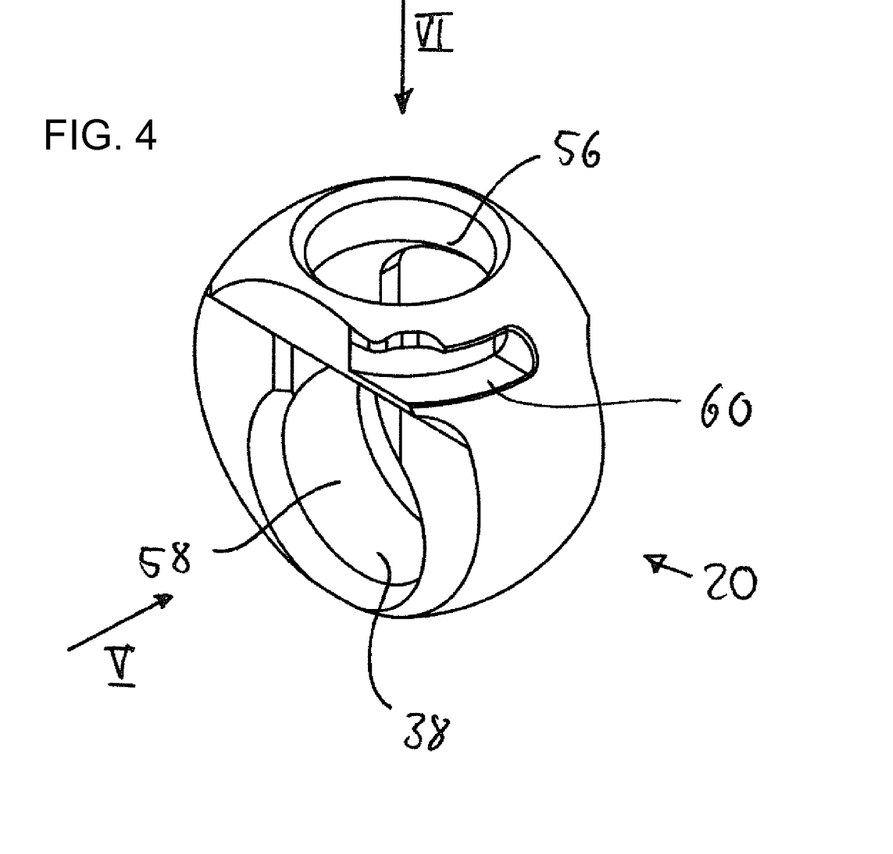
FIG. 4 shows a perspective view of the unassembled frame from FIG. 1.
Figure 5:
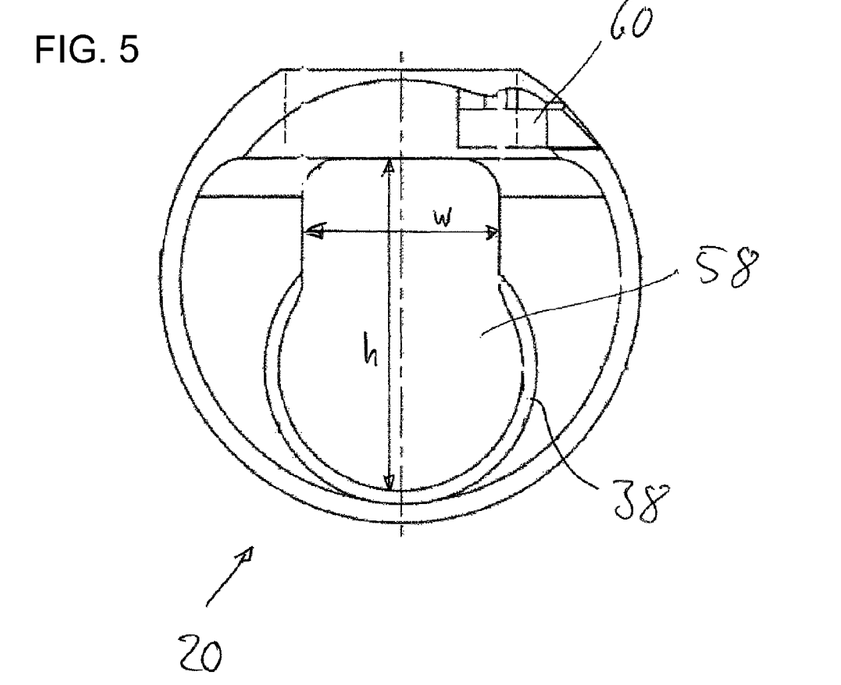
FIG. 5 shows the front view of the frame from FIG. 4 in the direction of the arrow V.
Figure 6:
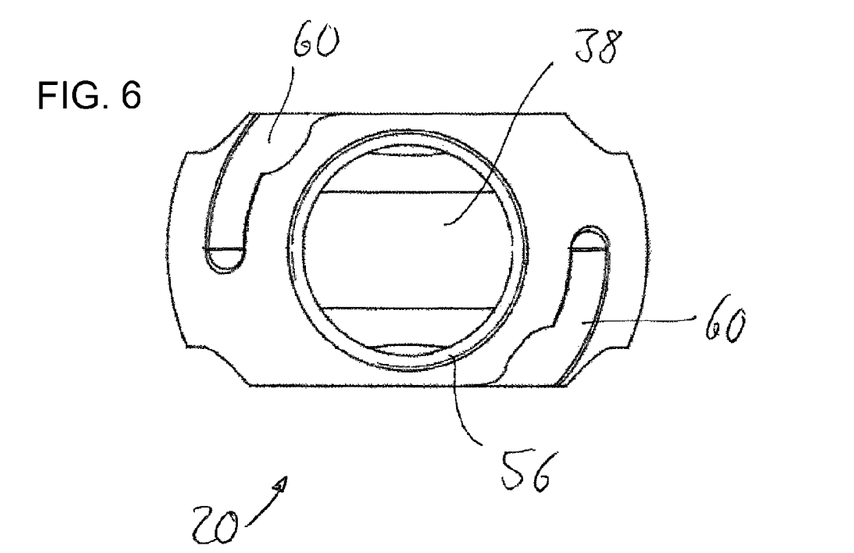
FIG. 6 shows the plan view of the frame from FIG. 4 in the direction of the arrow VI.

FIGS. 4-6 show the frame 20. In particular, they show the insert opening 58, through which the ball 22 is later introduced into the interior of the frame 20 and to bear on the inner surface 38. To be able to introduce the ball 22, the insert opening 58 has a clear width w and a height h, in each case greater than corresponding dimensions of the ball 22 (see FIG. 8).

A part of the interior of the frame 20 or of the insert opening 58 is the inner surface 38, formed as part of a sphere surface. The frame 20 has a threaded opening 56, into which the clamping element 26 is screwed.

On the outside of the frame 20, the threaded opening 58 is surrounded by a bayonet catch 60. The latter serves to grip the rod connector with the aid of a tool (not shown), e.g. a special holder, which engages on the bayonet catch 60.

Figure 7:
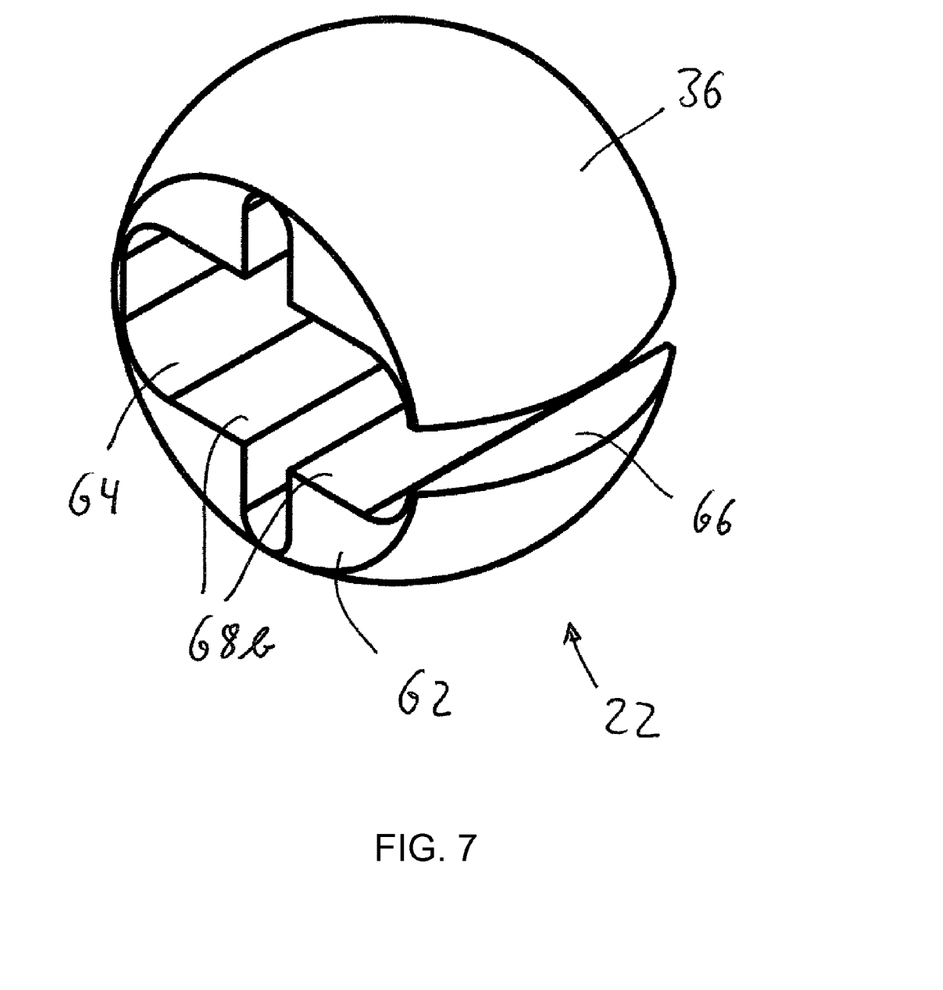
FIG. 7 shows a perspective view of the unassembled ball from FIG. 1.
Figure 8:
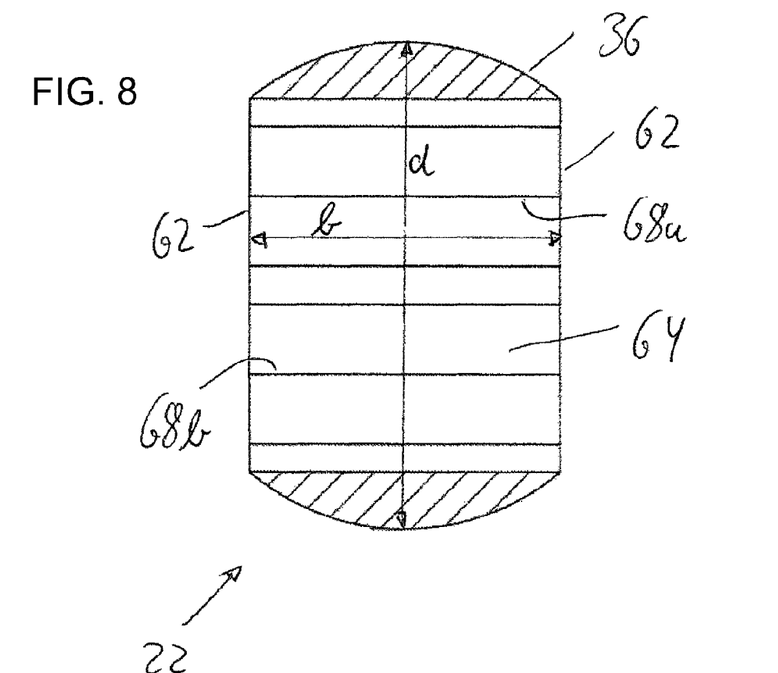
FIG. 8 shows a section through the ball from FIG. 7 in the direction of the arrow VIII-VIII in FIG. 9.
Figure 9:
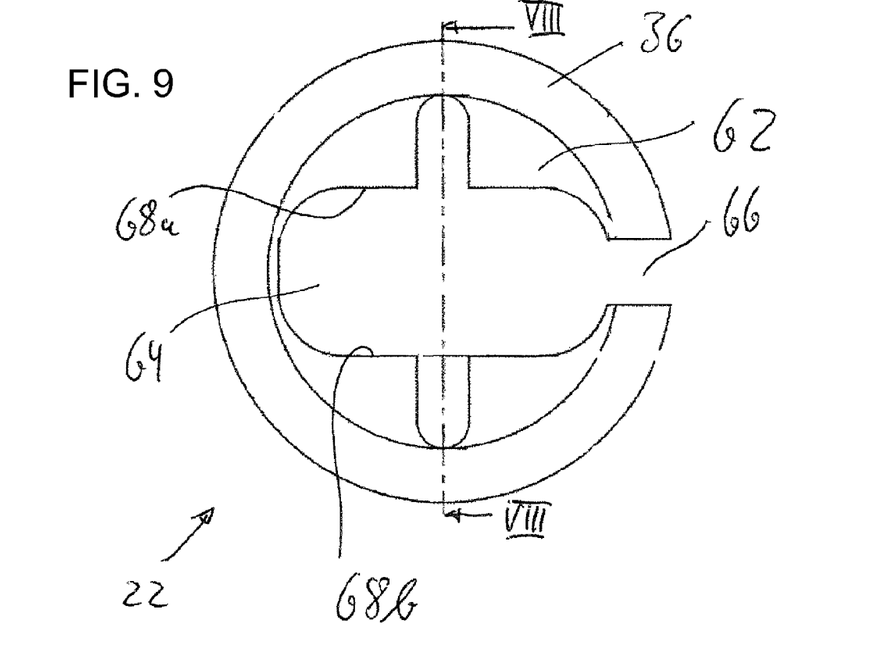
FIG. 9 shows the front view of the ball from FIG. 7 in the direction of the arrow IX.

FIGS. 7-9 show the ball 22 with its outer surface 36 shaped as part of a sphere. On two opposite sides, the ball 22 is in each case cut flat in the manner of a spherical layer, as a result of which two parallel flat surfaces 62 are obtained. These have a perpendicular distance to each other, i.e. the ball 22 has a width b. The width b is smaller than the abovementioned clear width w of the insert opening 58, such that the ball 22 can be pushed in a corresponding direction into the insert opening 58.

The greatest dimension of the ball 22 is its diameter d, which is dimensioned such that it is smaller than the height h of the insert opening 58. This is also necessary to ensure that the ball 22 can be introduced into the insert opening 58.

The ball 22 has a receiving space 64 into which, according to FIGS. 1 and 2, the branch 10 of the bracket 6b is inserted. In order to achieve the abovementioned clamping effect by pressure on the outer surface 36 in respect of the branch 10 lying inside the receiving space 64, the receiving space 64 is interrupted at the side by a gap 66. The two ball halves, which lie opposite each other in relation to a plane of symmetry of the ball 22 extending through the gap 66, can thus move with a spring action toward each other, as a result of which, when external pressure is applied to the ball 22, a clamping effect that fixes the branch 10 is obtained between the inner surfaces 68a,b.

Figure 10:
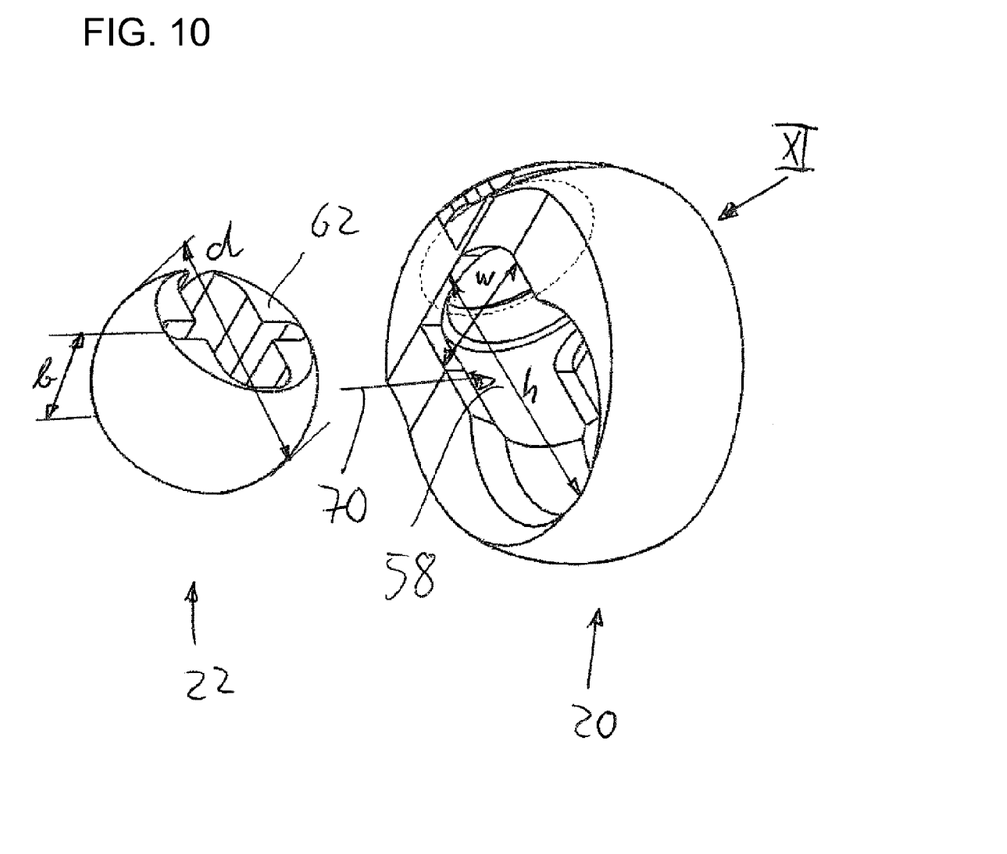
FIG. 10 shows a perspective view of the ball and frame in the assembly position.

FIGS. 10 to 14 show the assembly of the ball 22 into the frame 20 in chronological order. FIG. 10 shows the starting position for assembly, in which the ball 22 is oriented such that its flat surfaces 62 are oriented parallel to the insertion direction (direction of the arrow 70). To put it another way, the ball 22 lies such that the flat surfaces 62 are aligned with the direction of extension of the insert opening 58 in the frame 20. Since the width b is smaller than the width w and the diameter d is smaller than the height h, it is possible to move the ball 22 through the insert opening 58, in the direction of the arrow 70, into the interior of the frame 20.

Figure 11:
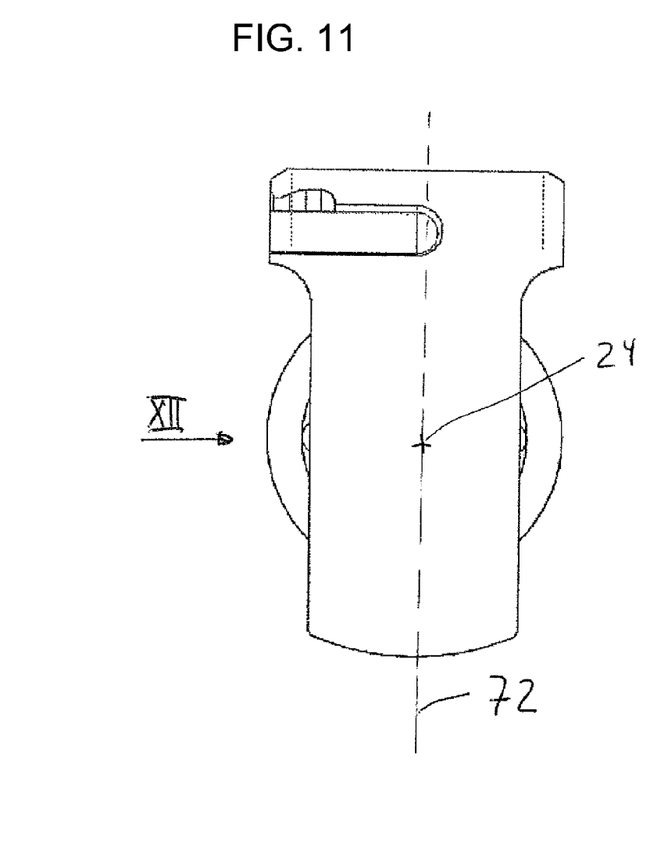
FIG. 11 shows the ball pushed into the frame, in the direction of the arrow XI in FIG. 10.
Figure 12:
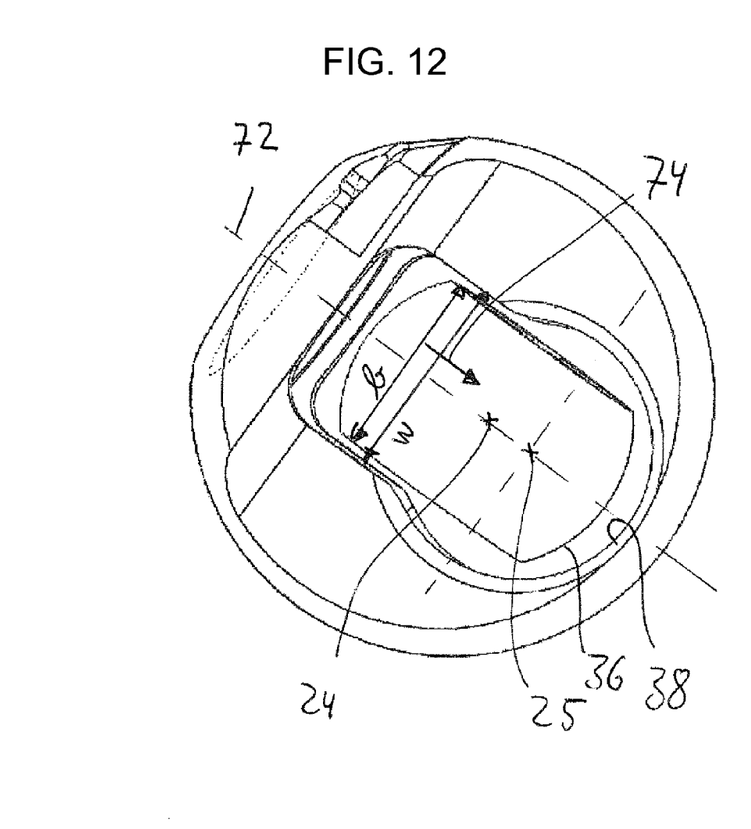
FIG. 12 shows the situation from FIG. 11 looking in the direction of the arrow XII.

FIGS. 11 and 12 show the situation after completion of the insertion procedure, i.e. when the center point 24 of the ball 22 is located at the center (indicated by the center axis 72) of the frame 20.

It will be seen from FIG. 12 that the ball 22 is inserted with its center point 24 slightly above the center point 25 of the sphere of the inner surface 38. Insertion is only possible in this way, since otherwise the outer surface 36 of the ball 22 would collide with the inner surface 38. Therefore, after complete insertion into the connection part 8, the center point 24 of the ball 22 is still located, on the center axis 72, above the center point 25 of the spherical inner surface 38.

Figure 13:
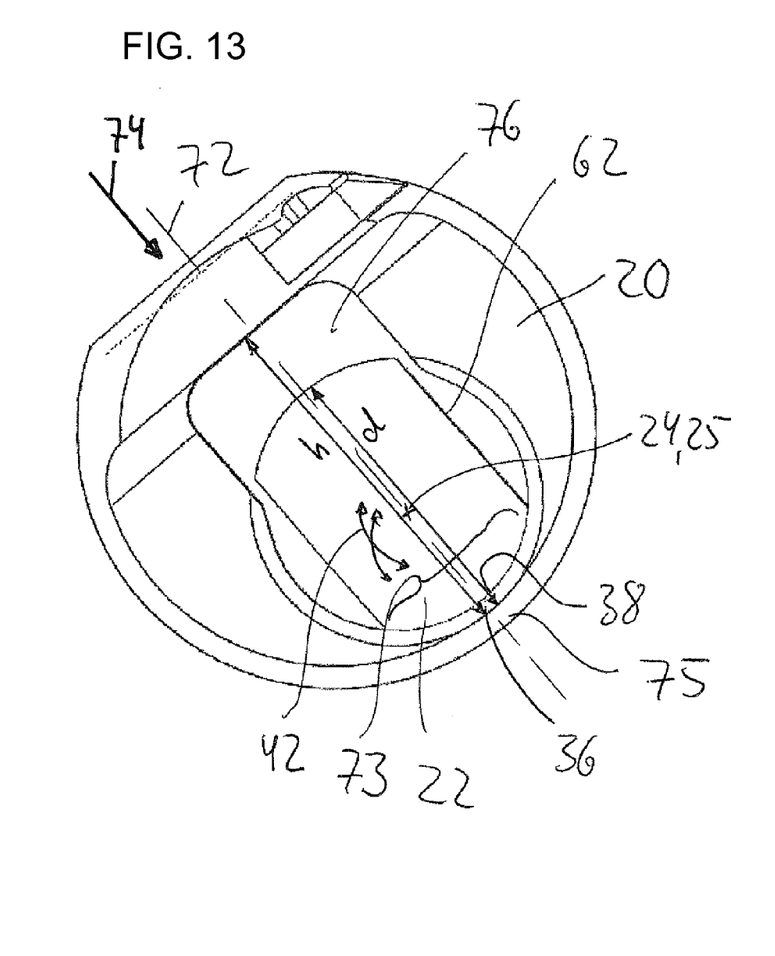
FIG. 13 shows the ball lowered into the inner surface compared to the situation illustrated in FIG. 12, and in a view according to FIG. 12.

FIG. 13 therefore shows the next assembly step: The ball 22 is lowered, in the direction of the arrow 74, along the center axis 72, until the outer surface 36 bears on the inner surface 38 on the underside 75 of the connection part 8. The lowering movement is possible since, on account of the still present rotation position of the ball 22, only a small area 73 of the outer surface 36 comes into contact with the inner surface 38, and the rest of the ball 22 has a sufficient distance or movement clearance from the inner surface 38. The center points 24 and 25 of ball 22 and inner surface 38 now coincide. Therefore, the ball 22 can now be rotated in any desired direction about the center point 24, 25. In doing this, large parts of the outer surface 36 slide onto the inner surface 38. In addition, above the ball 22, this also creates the receiving space 76 for receiving the branch 10, as shown in FIGS. 1 and 2. In the receiving space 76, the branch 10 is guided axially displaceably, likewise in the manner of a slide bearing, only in the direction of the arrow 40. Placing a branch 10 into the receiving space 76 with virtually no play also prevents the ball 22 moving counter to the direction of the arrow 74. Thus, the form fit enforced by the inner surface 38 can no longer be overcome, and the ball 22 is fixed in the connection part 8.

Figure 14:
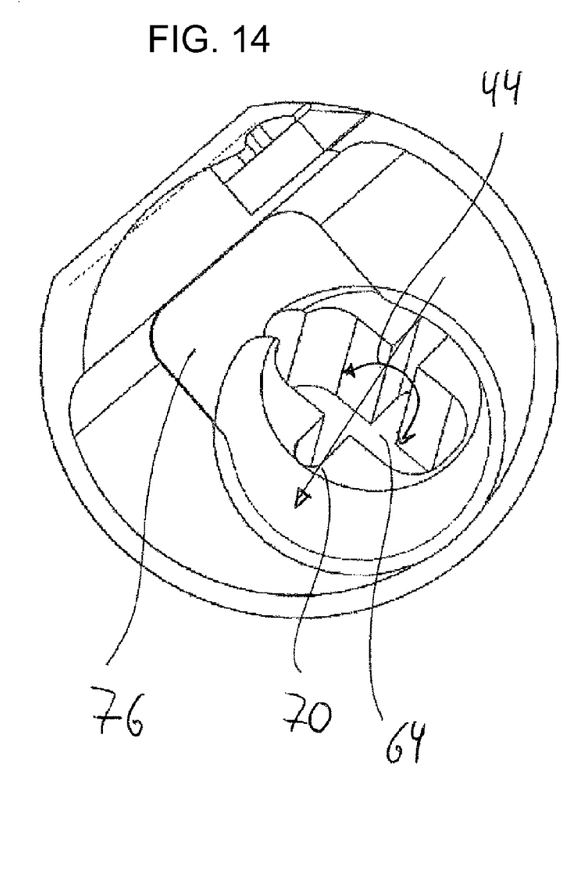
FIG. 14 shows the ball rotated compared to the situation from FIG. 13, and in a view according to FIG. 12.

FIG. 14 shows how in particular the ball 22 is rotated through approximately 90° about the center axis 72, such that the flat surfaces 62 now lie approximately parallel to the cross-sectional surface of the insert opening 58. Thus, the receiving space 64 is also accessible for receiving a first branch 10. The possible movements of the ball 22 are again indicated by the arrows 42 and the arrow 44. FIG. 14 now shows a relative position of ball 22 and frame 20, which position is rotated a further 90° in the direction of the arrow 44 compared to the position in FIGS. 1 and 2.

By rotating the ball 22 between the positions shown in FIGS. 13 and 14, the ball 22 in FIG. 14 is fixed in the inner surface 38, such that it is no longer movable in the direction of the arrow 70. To do so, it would also first have to be brought back to the position according to FIG. 13, i.e. with the flat surfaces 62 again oriented accordingly.

FIG. 15 again shows the loss prevention device 33 in detail in the state before assembly. It also shows, by way of example, the bracket 6a from FIG. 1, which has an opening 78 for receiving the fixing element 32, and an opening 82 for receiving the stop pin 37b. The figure shows in particular the collar 37a on the fixing element 32, and the stop pin 37b interacting therewith. First, the fixing element is screwed into the opening 80, until the collar 37a is recessed in the opening 78. The stop pin 37b is then fixed in the opening 82, e.g. by welding.

Figure 15:
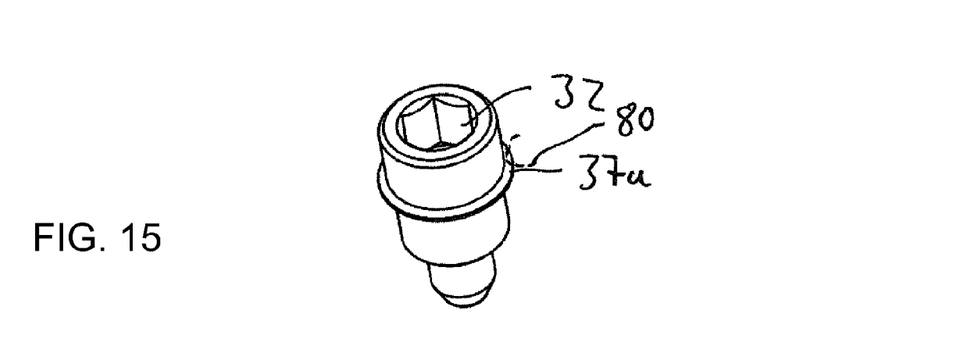
FIG. 15 is a perspective view of the loss prevention device.

The broken line 80 indicates that the stop pin 37b then covers the collar 37a. When the fixing element 32 is unscrewed, the collar 37a then strikes against the stop pin 37b, before the fixing element 32 can leave the opening 78, and is thus permanently held there.

The invention claimed is:

1. A rod connector for a transverse connection of two vertebral column rods, the rod connector comprising:
    first and second clamps each for partially enclosing and securing a respective vertebral column rod in an assembly state thereof, each said clamp including a main support with a stationary clamping jaw and a spring jaw mounted resiliently on said main support;
    a transverse bridge for fixing said clamps relative to each other, said transverse bridge including a first branch mounted on said first clamp, a second branch mounted on said second clamp, and a connection part connecting said first and second branches;
    a spring mechanism for each said clamp, said spring mechanism having a spring force with a value that is low enough to enable said clamp to be snapped manually onto the vertebral column rod, to be displaced thereon in the assembly state, and to be released therefrom; and
    a fixing mechanism for each said clamp, said fixing mechanism being capable of actuation independently of said spring mechanism and having a holding force high enough to solidly fix said clamp on the vertebral column rod in the assembly state, said fixing mechanism having a fixing element preventing a pivot-opening of said clamp, said fixing element being a threaded pin screwed into said clamp for pressing on a side of said spring jaw facing away from said stationary clamp jaw and pressing said vertebral column rod against said stationary jaw for finally fixing said vertebral column rod.

2. The rod connector according to claim 1, wherein said spring mechanism is a spring bridge connecting said spring jaw to said main support.

3. The rod connector according to claim 2, wherein said spring jaw, said spring bridge, and said main support are formed in one piece.

4. The rod connector according to claim 3, wherein at least one of said spring jaw or said spring bridge is cut out from said main support.

5. The rod connector according to claim 1, wherein said spring jaw and said main support each have a form-fit element, and said form-fit elements have play between each other in respect of the spring mechanism and are movable into each other with a form fit by said fixing mechanism.

6. The rod connector according to claim 5, wherein said form-fit elements are formed with faces directed toward each other, and said faces have a substantially S-shaped matching form.

7. A rod connector for a transverse connection of two vertebral column rods, the rod connector comprising:
    first and second clamps each for partially enclosing and securing a respective vertebral column rod in an assembly state thereof;
    a transverse bridge for fixing said clamps relative to each other, said transverse bridge including a first branch mounted on said first clamp, a second branch mounted on said second clamp, and a connection part connecting said first and second branches;
    said connection part having a frame for receiving said first branch, a ball rotatably mounted in said frame and having said second branch pass therethrough, and a locking device acting on said first and second branches, said first branch passing through a receiving space formed between said ball and said frame, an outer surface of said ball cooperating with a ball-shaped inner surface of said frame as a slide pairing;
    a spring mechanism for each said clamp, said spring mechanism having a spring force with a value that is low enough to enable said clamp to be snapped manually onto the vertebral column rod, to be displaced thereon in the assembly state, and to be released therefrom; and
    a fixing mechanism for each said clamp, said fixing mechanism being capable of actuation independently of said spring mechanism and having a holding force high enough to solidly fix said clamp on the vertebral column rod in the assembly state.

8. The rod connector according to claim 7, wherein said locking device generates a locking frictional engagement between said branches and said connection part.

9. The rod connector according to claim 8, wherein said ball is formed with a gap that is compressible for locking the second branch.

10. The rod connector according to claim 8, wherein said locking device comprises a clamping element configured to bear on said frame and pressing said first branch against said ball.

11. The rod connector according to claim 7, wherein said first branch has an underside facing said outer surface of said ball and has a circular cross-section to bear on said outer surface of said ball, a radius of said circular cross-section is selected to conform to a radius of said ball.

* * * * *